(12) United States Patent
Danylewych-May et al.

(10) Patent No.: US 6,446,514 B1
(45) Date of Patent: Sep. 10, 2002

(54) COMBINED PARTICLE/VAPOR SAMPLER

(75) Inventors: Ludmila Danylewych-May, North York; John Henry Davies, Mississauga; Frank Kuja, Brampton; Sabatino Nacson, Thornhill, all of (CA)

(73) Assignee: Barringer Research Limited, Mississauga (CA)

( * ) Notice: Subject to any disclaimer, the term of this patent is extended or adjusted under 35 U.S.C. 154(b) by 0 days.

(21) Appl. No.: 09/484,257

(22) Filed: Jan. 18, 2000

(51) Int. Cl.⁷ .............................. G01N 1/22; G01N 1/08
(52) U.S. Cl. ................... 73/863.21; 73/864.71; 73/863.12; 73/863.23; 73/863.31
(58) Field of Search .................. 73/863.21, 864.71, 73/863.02, 863.03, 863.23, 863.24, 863.25, 863.31, 863.33, 864.34, 863.12

(56) References Cited

U.S. PATENT DOCUMENTS

| | | | | |
|---|---|---|---|---|
| 3,925,022 A | * | 12/1975 | Showalter et al. ............ 73/23.2 |
| 3,933,431 A | * | 1/1976 | Trujillo et al. ....... 73/863.21 X |
| 3,970,428 A | * | 7/1976 | Barringer ................. 73/863.22 |
| 4,192,176 A | * | 3/1980 | Barringer ................... 73/28.04 |
| 4,220,414 A | * | 9/1980 | Barringer .................... 356/318 |
| 4,909,090 A | * | 3/1990 | McGown et al. .... 73/863.12 X |
| 5,162,652 A | * | 11/1992 | Cohen et al. ......... 73/863.21 X |
| 5,212,991 A | * | 5/1993 | Suzanne et al. ...... 73/864.71 X |
| 5,425,263 A | * | 6/1995 | Davies et al. ............... 73/28.05 |
| 5,476,794 A | * | 12/1995 | O'Brien et al. ................ 436/92 |
| 5,693,895 A | * | 12/1997 | Baxter ................. 73/864.71 X |
| 5,753,832 A | * | 5/1998 | Bromberg et al. ........ 73/864.81 |
| 5,859,375 A | * | 1/1999 | Danylewych -May et al. .............. 73/864.71 |

FOREIGN PATENT DOCUMENTS

| | | | | |
|---|---|---|---|---|
| GB | 2169078 A | * | 7/1986 | ............... 73/863.12 |
| JP | 6-221970 | * | 8/1994 | ................. 73/23.2 |

* cited by examiner

*Primary Examiner*—Thomas P. Noland
(74) *Attorney, Agent, or Firm*—Bereskin & Parr

(57) ABSTRACT

An method of, and an apparatus for, collecting a sample of a substance of interest, utilizes an apparatus having a device for collecting a vapor sample and a device for retaining a substrate. A substrate, having a working portion and a mounting portion, is mounted by the mounting portion of the substrate, whereby the working portion of the substrate is exposed for use. The apparatus so that the working portion of the substrate traverses surfaces of interest, to collect a particulate sample. A device for sampling vapor is operated to obtain a vapor sample. The vapor and particulate samples collected are analyzed.

17 Claims, 5 Drawing Sheets

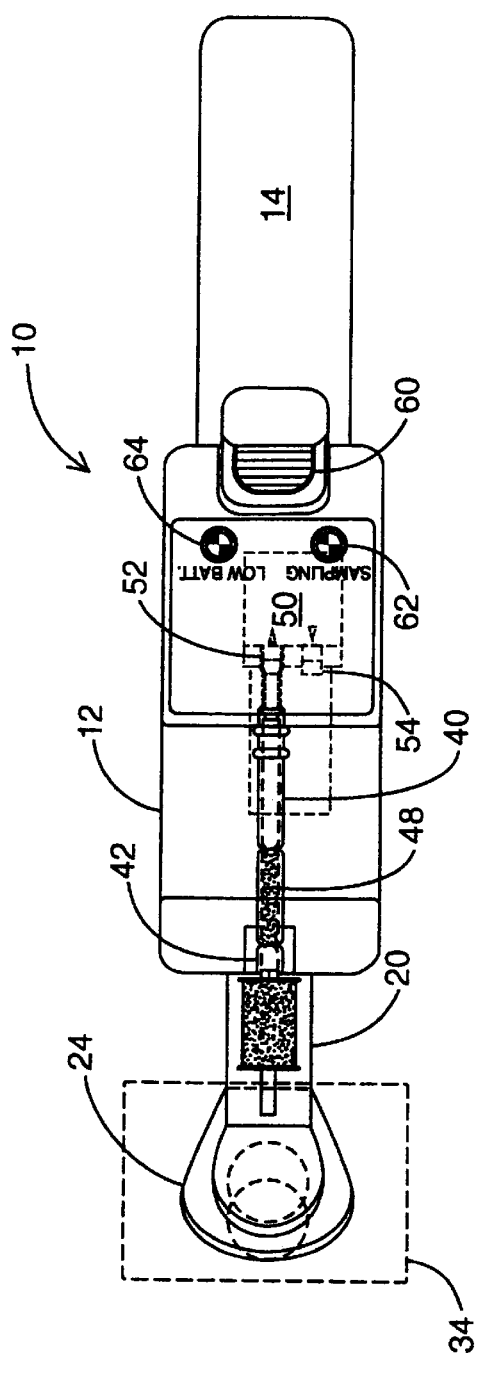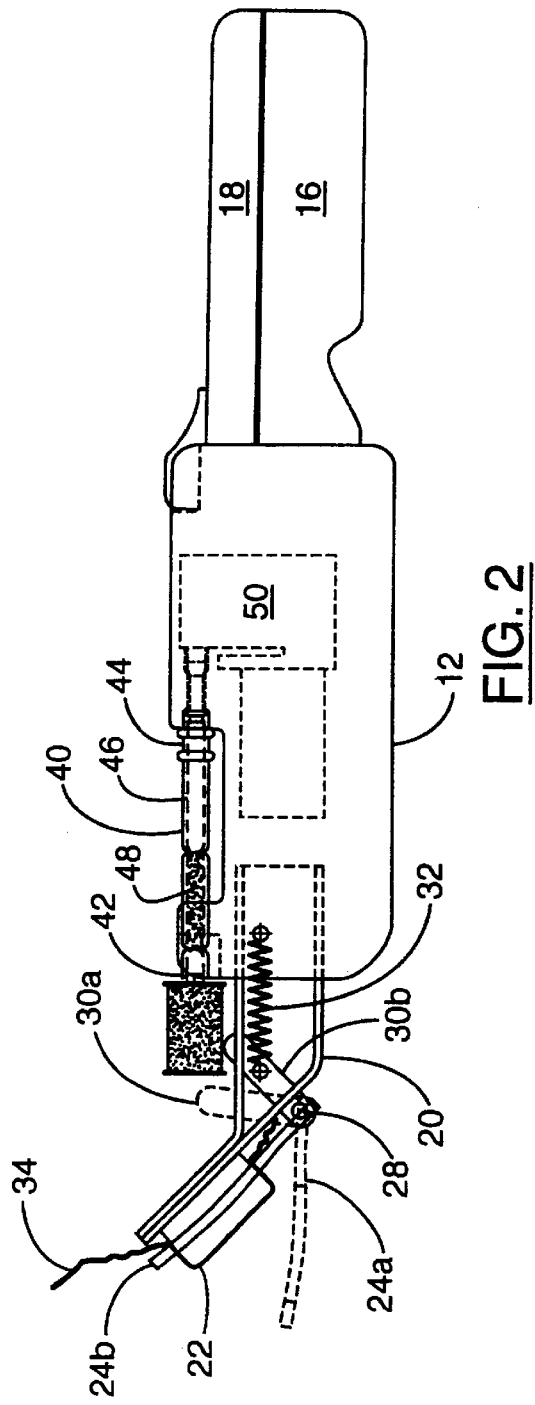

COMBINED PARTICLE/VAPOR SAMPLER

FIELD OF THE INVENTION

This invention relates to the collection from surfaces of samples of trace particles or liquids, or other compounds, and vapours thereof, for chemical detection by various analytical means, such as an ion mobility spectrometer (IMS), gas chromatography (GC), liquid chromatography (LC), mass spectrometry (MS) and other methods, the compounds being present either as traces within particles or as discrete particles or aerosols, droplets or the like, or as vapours. The invention more particularly relates to the detection of explosives, narcotics, and other contraband concealed by individuals in their belongings or in transported goods and cargo, or in vehicles and aircraft. However, the invention also encompasses environmental sampling such as chemical warfare agent liquid droplets and aerosols which are extremely toxic and for which no hand contact can be tolerated.

BACKGROUND OF THE INVENTION

The removal of dust as a simple household task from domestic dwellings has been and is still carried out with dust cloths. In more sophisticated situations, chatelaines and housekeepers have employed maids, butlers and valets equipped with white gloves or mittens to remove dust, polish silverware and furniture. Previously, there has been no necessity or interest in analyzing the collected dust particles. Rather, the sole intent was to collect and throw out dust and dirt particles.

The necessity to collect dust and particles for analysis is a more recent requirement. With the advent of terrorism where explosives can be concealed to create undetectable bombs and also with drug smugglers concealing their drug shipments, the need for trace/forensic detection has become necessary. While early explosives detectors relied on the collection of atmospheric explosives vapours, modern high power explosives are plastic with extremely low vapour pressures thereby presenting vapour detection instruments with extremely difficult detection situations to the point of impossibility. Modern plastic explosives can have vapour pressures 5 or 6 orders of magnitude lower than the traditional volatile explosives such as nitroglycerine (NG), trinitrotoluene (TNT) and ethylene glycol denitrate (EGDN). For example, U.S. Pat. No. 4,909,090 teaches the use of hand operated vapour samplers which heats the surface to assist in dislodging vapours which are trapped on collector surfaces in the probe. However, with the very low vapour pressure of plastic explosives and drugs this method is extremely limited in its usefulness. Drugs like cocaine, heroine and others also have very low vapour pressures and thus are undetectable by existing vapour detection instruments.

Modern detection equipment can detect extremely low levels of explosives, narcotics and the like, in the range of nanograms or picograms However, this simply raises the problem of obtaining a suitable sample. Accordingly, rather than attempt to collect a vapour sample, an alternative approach of particle collection and analysis was proposed, notably by Barringer, et al, and followed by others, both for forensics purposes as well as for surface geochemical exploration where trace metals and organometals can be useful as pathfinder indicators in mineral exploration activities. Earlier patents have covered these applications, such as Barringer U.S. Pat. Nos. 3,970,428; 4,220,414; 4,192,176; and 5,425,263.

Particle collection techniques include: surface inspection by means of physical particle collection in minute amounts; the use of dust pan-brush arrangements; vacuum suction onto porous or semi-porous substrates, filters, membranes and the like; the use of swabs, swipes, gloves, etc. One such method is described in U.S. Pat. No. 5,476,794 which describes the removal of particles with a glove and the use of an intermediate step, that of vacuum suction off the glove. Applicant's own earlier U.S. Pat. No. 5,425,263 discloses an apparatus and method for collecting a sample of particles or droplets, or a substrate, for analysis in an IMS device or the like. These techniques have been the subject of earlier patents, which have developed into more sophisticated techniques incorporated into various instrumental devices for direct analysis, including plasma optical emission spectrometers, optical analyzers and mass spectrometers among others.

Gloves, mitts and swipes have been used in various forms for particle collection. Disadvantages exist with these earlier systems of collection. The major disadvantage of most of these earlier techniques is that an intermediate step is required to transfer from such a glove or the like any particles/trace chemicals so collected for presentation to the analytical device. One method is to use a suction device to vacuum the glove or mitt, as in U.S. Pat. No. 5,476,794.

Applicant's earlier U.S. Pat. No. 5,859,375 was intended to overcome many of the problems in this art, relating to collection of particles/vapours. It provided a technique for quickly and simply collecting a sample directly onto a substrate, while eliminating, or at least significantly reducing, the problems of cross-contamination between a sample or contamination of a user's hands.

However, in this earlier technique, there was no way of collecting just a vapour sample. Some substances of interest have a significant vapour pressure at ambient temperatures, yet are difficult to collect as particles and/or droplets.

The surfaces of objects which are contaminated with explosives, drugs, or other chemicals, frequently retain traces of these substances in the form of small particles, and, if the substances in question have an appreciable vapour pressure, the objects evolve small amounts of chemical vapour. If the surfaces of such objects are swabbed with a suitably chosen material, as in the patents mentioned above, some of the particles will adhere to the swab.

Similarly, if a sample of air is aspirated from close to the surface of the object, through a cartridge containing an appropriate sorbent, some of the vapour of the target chemicals will be retained. The chemicals can then be detected by inserting the swab and the cartridge into suitable analytical apparatus, such as an Ion Mobility Spectrometer (IMS) equipped with a pyrolyser/desorber. Collecting both particles and vapour extends the range of compounds which can be detected, increases the probability of detection, and reduces the false alarm rate. The circumstances in which objects are to be screened for concealed contraband, such as drugs or explosives, dictate that the objects be processed rapidly, and also that samples be obtained from interior surfaces of vehicles and other large structures. The present invention addresses these needs by providing a device which combines both sampling modalities in a unit which can be carried and operated with one hand. It has the further advantage that it may be configured to have extended length and minimal diameter, extending the effective reach of the operator into otherwise inaccessible or dangerous or contaminated areas.

Techniques that rely on particle collection by vacuum suction and the like require a high air flow rate to efficiently dislodge particles from a surface, so that a collector using this method is larger, heavier, and less convenient to use than the present invention. U.S. Pat. No. 3,925,022 teaches the use of an absorbent to pre-concentrate vapours prior to detection, but the apparatus described is integral with the analyzer used for detection and not portable, nor does it provide collection of particles. U.S. Pat. No. 5,753,832 describes an apparatus for collection of both particles and vapour, but uses a single conduit and airflow. Since the optimum air flows for particle and vapour collection are very different, this apparatus must use an airflow rate which is a compromise, resulting in reduced collection efficiency for at least one of the phases. In addition, it requires an umbilical hose connection from the sampling point to the analyzer. This makes use more difficult, and also is subject to loss of both particle and vapour by adhesion to the walls of the hose, leading to loss of detection sensitivity, and to false alarms following a genuine detection, due to release of target analyte trapped on the walls of the hose.

SUMMARY OF THE INVENTION

In accordance with a first aspect of the present invention, there is provided a sampling apparatus, capable of collecting both a particulate sample and a vapour sample, the sampling apparatus comprising:

a main body;

a retaining means on the main body for retaining a substrate, for passing the substrate over surfaces of interest to collect a particulate sample for analysis; and a vapour sample collection means including an absorbent material, for absorbing a vapour sample from air passing over the absorbent material, for later desorption and analysis.

Preferably, the apparatus includes a head and a retaining means for retaining one portion of the substrate and for presenting another portion of the substrate for contact with surfaces of interest, for particulate collection.

The vapour sampling means can include a removable cartridge, the cartridge comprising a body, said absorbent material being located within the body, an inlet for air and an outlet; and a pumping means connectable to the outlet of the cartridge for pumping air through the cartridge.

Advantageously, the absorbent material is located within a working portion of the cartridge, and the absorbent material has a large surface area for contact with air, whereby, in use, air is caused to pass over the surface of the absorbent material, for absorption of vapours. Moreover, the cartridge is conveniently generally elongate and tubular.

The vapour sampling means advantageously includes two or more working portions, each provided with a respective absorbent material, and the working portions can be arranged for air to flow sequentially through the working portions.

Alternatively, the working portions are arranged in parallel and connected in parallel between the inlet and the outlet of the cartridge, with each working portion having a respective, separate air flow therethrough.

Conveniently, the substrate provides the particulate filter for the vapour sampling means.

The apparatus can include means for bypassing the substrate and enabling air to be drawn directly into the inlet of the cartridge.

More preferably, the apparatus includes a head and the retaining means mounted on the head, and the retaining means comprises a boss mounted on the head, and a plate including a central bore, wherein the plate is moveable between an open configuration spaced from the boss to permit mounting and removal of a substrate and a closed position in which the boss projects through the central bore of the plate, to retain a substrate by an edge portion thereof, with the boss causing a central, working portion of the substrate to project outwardly.

Preferably, the substrate is chemically inert, is devoid of any dyes and colouring materials, and is such as to be capable of a mechanical wiping action, without removing from the substrate appreciable amount of lints and fibres. For example, the substrate can be woven and can comprise one of cotton, polytetrafluoroethylene, and fibreglass.

In one variant, the substrate is chemically treated to enhance its ability to collect and entrap at least one of desired particles, droplets and chemical agents, and wherein the substrate has been chemically treated to modify the chemistry thereof during desorption or pyrolysis cycles.

Another aspect of the present invention provides a method of collecting a sample of a substance of interest, the method comprising the steps of:

(1) providing an apparatus having means for collecting a vapour sample and retaining means for retaining a substrate;

(2) providing a substrate having a working portion and a mounting portion, and mounting the substrate by the mounting portion of the substrate, whereby the working portion of the substrate is exposed for use;

(3) manipulating the apparatus so that the working portion of the substrate traverses surfaces of interest;

(4) operating the vapour sampling means to obtain a vapour sample; and (5) analyzing the vapour sample collected by the vapour sampling means and a particulate sample collected on the substrate.

The method preferably includes providing the vapour sampling means with a cartridge including an absorbent material adapted to absorb a vapour sample from air flow therethrough, and step (4) then comprises passing air through the cartridge to generate a vapour sample on the absorbent material within the cartridge.

More preferably, step (5) comprises, for the substrate, releasing the substrate from the retaining means, mounting the substrate in an analyzer and causing particulates on the substrate to be released and/or desorbed, and for the vapour sample, the method comprising removing the cartridge from the sampling apparatus, mounting the cartridge in an analyzer, and causing the vapour samples to be released from the absorbent material.

Advantageously, for the particulate sample, the substrate is mounted in an analyzer and heated to cause desorption of vapours from particulates on the substrate, and for the vapour sample, the cartridge is heated to cause desorption of the vapour sample from the absorbent material.

The method can be applied to the detection of at least one of drugs, explosives, chemical warfare agents and biological warfare agents. For example, the can be applied to detecting at least one of drugs, explosives, ICAO taggants for explosives, chemical warfare agents, chemical warfare agent precursors, biological warfare agents and the like.

Preferably, the method includes controlling the vapour sampling means, whereby the flow rate of air and the duration of a sampling is sufficient to ensure the collection of a sufficient amount of vapour sample on the absorbent material.

BRIEF DESCRIPTION OF THE DRAWINGS

For a better understanding of the present invention, reference is made, by way of example, to the accompanying Drawings, which show a preferred embodiment of the invention, and in which:

FIG. 1 is a top view of the exterior of a sampling apparatus in accordance with the present invention;

FIG. 2 is a side view of the exterior of a sampling apparatus in accordance with the present invention;

DESCRIPTION OF THE PREFERRED EMBODIMENTS

Figure 3:
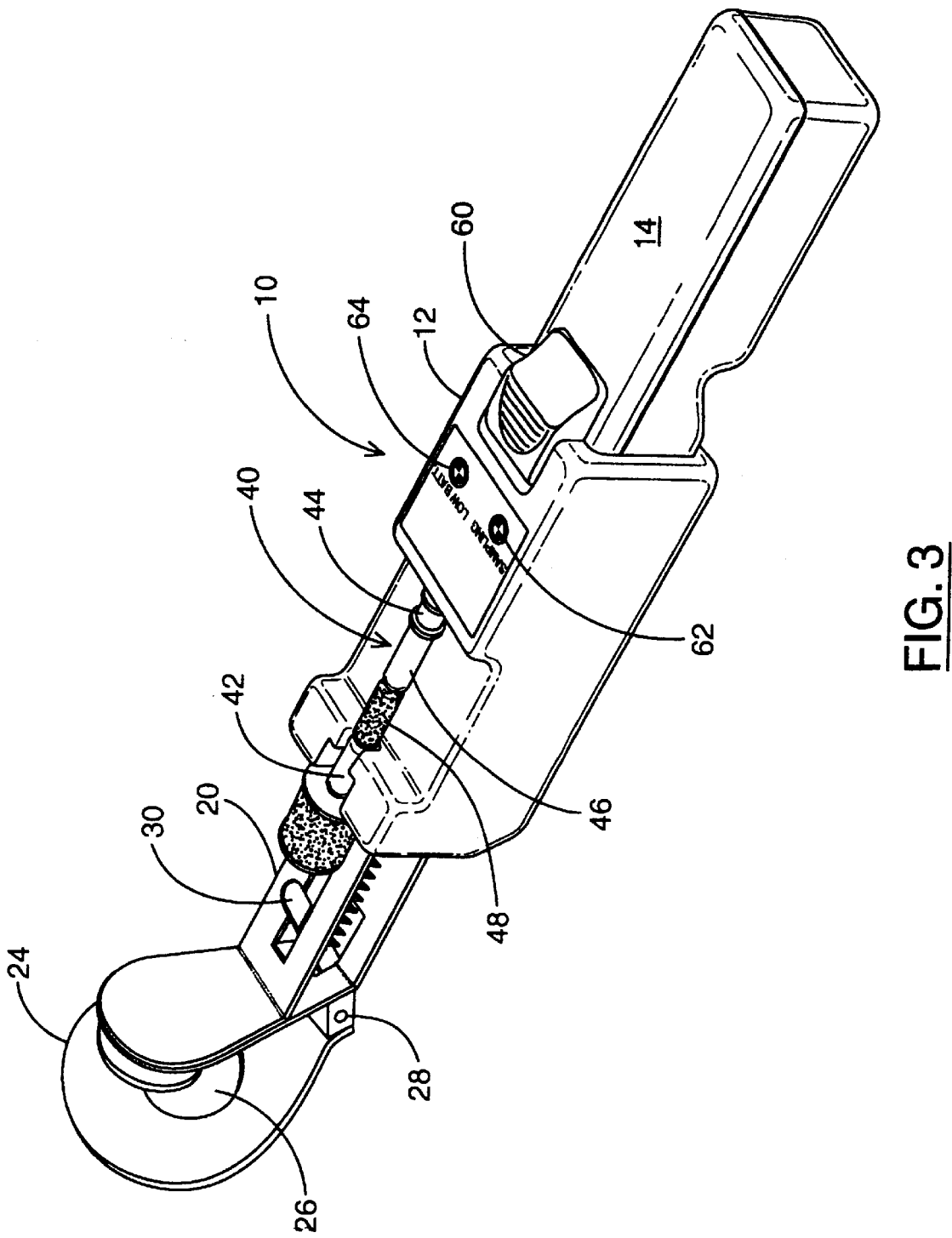
FIG. 3 is perspective view of the exterior of a sampling apparatus of FIGS. 1 and 2.
Figure 4:
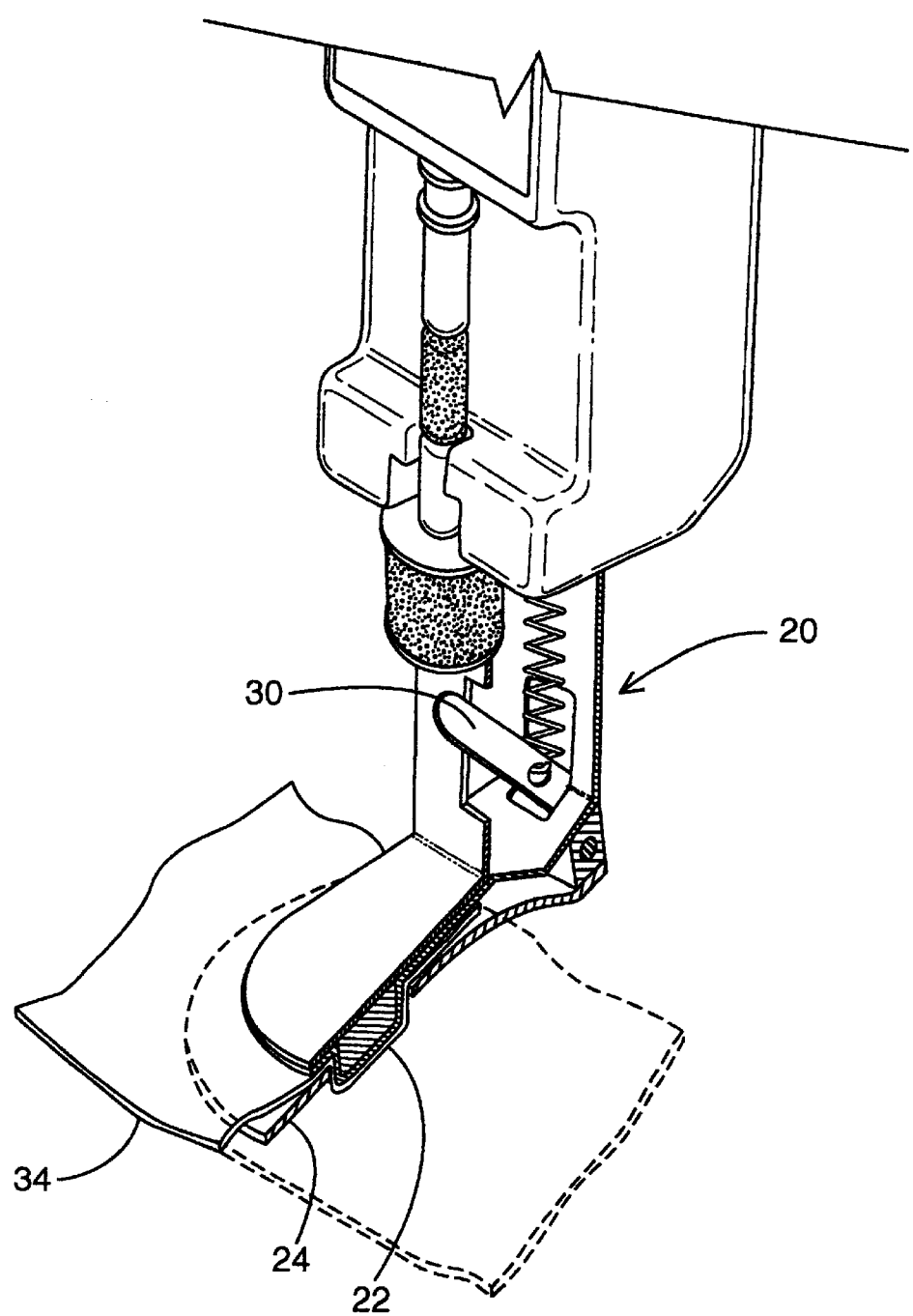
FIG. 4 is a partial cut-away view of the distal end of the invention showing the means of retaining the swab.
Figure 5:
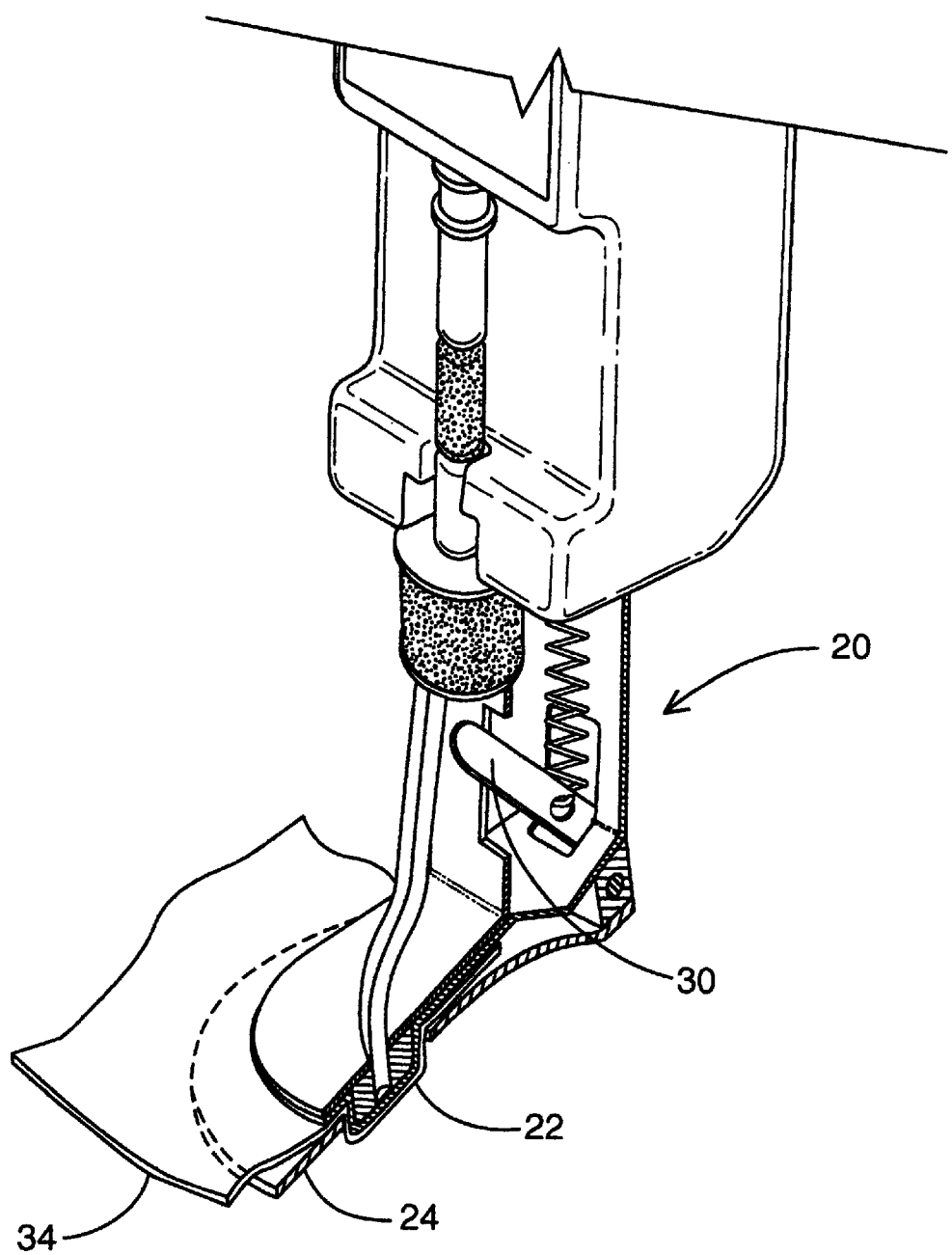
FIG. 5 is the same view as FIG. 4, but illustrating a variant, wherein the vapour sample is drawn through the swab.

An apparatus in accordance with the present invention is indicated generally by the reference 10. The apparatus 10 includes a main body 12. Extending out from one end of the main body is an apparatus or sampler handle 14. As indicated at 16 and 18 in FIG. 2, the handle 14 is configured to provide a compartment 16 for batteries and a compartment 18 for spare swabs and special vapour cartridges.

Extending out from the other or forward end of the body 12 is a head 20. Mounted on the head 20 is a boss 22. A retaining means 24 comprises a plate, which is dished slightly as shown and which includes a central bore 26.

The plate 24, providing the retaining means, is pivotally mounted to the head 20 at 28. A lever 30 is secured to the plate 24. A spring 32 is connected between the lever 30 and the head 20.

FIG. 2 shows an open configuration of the plate 24 and lever 30 indicated as 24a, 30a and a closed configuration indicated at 24b, 30b. The spring 32 is a tension spring, so as to bias the plate into the closed position 24b.

In use, in accordance with applicant's earlier U.S. Pat. No. 5,859,375, a generally sheetform substrate or swab 34 would be mounted around the boss 22 and retained by the plate 24 at its edges. This then presents a central, working portion of the swab or substrate 34, for wiping over surfaces of interest to collect particles.

Figure 6A:
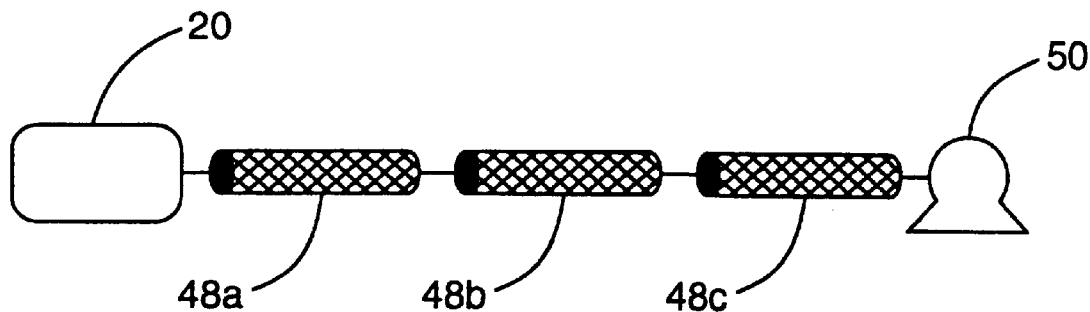
FIG. 6A is a schematic view of a vapour cartridge according to an alternative embodiment of the invention.

Now in accordance with the present invention, there is additionally provided means for collecting a vapour sample. In this specific embodiment, this comprises a vapour cartridge 40. The cartridge 40 includes an inlet 42 and an outlet 44, the cartridge 40 has a generally tubular body 46, which is shown, as two narrow throat portions, defining the ends of a main working portion 48. Within the working portion 48, there is a suitable absorbent material. The absorbent material is selected so as to be capable of absorbing vapours or a substance of interest from air flow through the cartridge 40. If desired, two or more different materials can be provided, each in its own working portion 48a–c, sequentially within the cartridge 40, as shown in FIG. 6A. The absorbent material could be a carrier material coated with a suitable chemical, for example activated carbon.

Figure 6B:
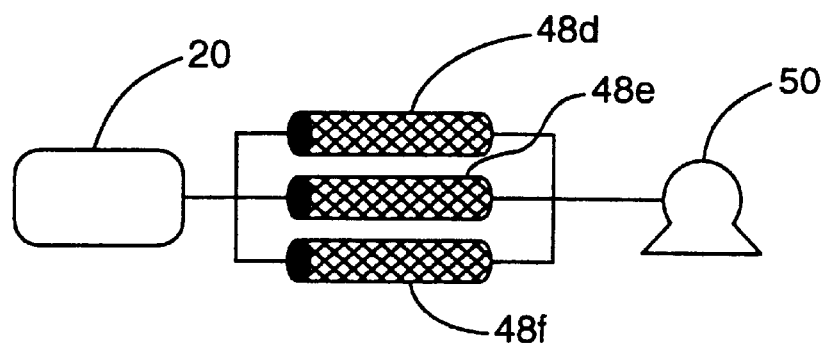
FIG. 6B is a schematic view of the cartridge according to a second alternative embodiment of the invention.

Alternatively, depending upon the substances to be detected, one can provide full parallel detection of substances of interest. Thus, there could be a number of parallel working portions 48d–f mounted to have an appropriate air flow therethrough, as shown in FIG. 6B. Alternatively, there could be a number of parallel vapour cartridges all mounted to have an appropriate air flow therethrough.

Air is drawn through the cartridge 40 by means of a pump 50, provided with an inlet connection 52 and an exhaust 54. Where parallel cartridges are provided, then some means would be provided for connecting them together, to the inlet of the pump 50.

In terms of operational controls, a switch 60 is provided for actuating the pump 50. A visual indication, for example an LED 62 is provided, to confirm operation of the pump 50. Additionally, there is another LED or light 64, for giving a warning of a low battery condition.

In use, a swab or substrate 34 is fitted to the head 20, by moving the plate 24 to the open position 24a, and then releasing it, so that swab 34 is held in the closed position 24b. The apparatus 10 can then be grasped and the central portion of the substrate 34 run over surfaces of interest, for example the outside of suitcases, other articles of luggage, the inside of vehicles (whether land, sea or air vehicles).

In accordance with the present invention, simultaneously, the pump 50 can be actuated, to draw in a vapour sample into the cartridge 40.

Once the particular examination has been completed, then, as described in applicant's earlier U.S. Pat. No. 5,859, 375, the plate 24 is displaced to the open configuration, to release the substrate 34. The substrate 34, grasped just by its edges, is transferred to an ion mass analyzer or the like, for desorption of particles collected thereon, and hence analysis of vapours given off by those particles. In an ion mass analyzer, this is done by heating the substrate to vaporize and pyrolyse the particles.

The cartridge 40 is also removed and transferred to an analyzer for analysis. Again, the absorbent material within the working portion 48 is selected to be capable of withstanding elevated temperatures. It is similarly heated, to cause desorption of vapours on the absorbent material and/or to pyrolyse these vapours. At the same time, a flushing gas is passed through the cartridge 40 to pass the sample into an analyzer for analysis. Other methods and materials could be used, e.g. known techniques based on solvent extraction, but the disclosed technique is preferred for use by unsophisticated operatives under field conditions.

What is claimed is:

1. A sampling apparatus, capable of collecting both a particulate sample and a vapour sample, the sampling apparatus comprising:

a main body;

a retaining means on the main body for retaining a substrate, for passing the substrate over surfaces of interest to collect a particulate sample for analysis; and a vapour sample collection means including an absorbent material, for absorbing a vapour sample from air passing over the absorbent material, for later desorption and analysis, the vapour sample collection means including a removable cartridge, the cartridge comprising a body, said absorbent material being located within the body, an inlet for air and an outlet; and a pumping means connectable to the outlet of the cartridge for pumping air through the cartridge.

2. A sampling apparatus as claimed in claim 1, which comprises a head and a retaining means for retaining one portion of the substrate and for presenting another portion of the substrate for contact with surfaces of interest, for particulate collection.

3. An apparatus as claimed in claim 2, wherein the absorbent material is located within a working portion of the cartridge, and the absorbent material presents a large surface area for contact with air, whereby, in use, air is caused to pass over the surface of the absorbent material, for absorption of vapours.

4. A sampling apparatus as claimed in claim 3, wherein the cartridge is generally elongate and tubular.

5. A sampling apparatus as claimed in claim 3 or 4, wherein the absorbent material comprises a carrier coated with activated carbon.

6. A sampling apparatus as claimed in claim 2, including a particulate filter provided upstream of the cartridge, for trapping particles, thereby to prevent contamination of the absorbent material by particles.

7. A sampling apparatus as claimed in claim 6, wherein the substrate provides the particulate filter for the vapour sampling means.

8. A sampling apparatus as claimed in claim 7, including means for bypassing the substrate and enabling air to be drawn directly into the inlet of the cartridge.

9. A sampling apparatus as claimed in claim 2, wherein the vapour sampling means includes two or more working portions, each provided with a respective absorbent material.

10. A sampling apparatus as claimed in claim 9, wherein said working portions are arranged for air to flow sequentially through the working portions.

11. A sampling apparatus as claimed in claim 9, wherein the working portions are arranged in parallel and connected in parallel between the inlet and the outlet of the cartridge, with each working portion having a respective, separate air flow therethrough.

12. A sampling apparatus as claimed in claim 2, wherein the apparatus includes a head and the retaining means is mounted on the head, and wherein the retaining means comprises a boss mounted on the head, and a plate including a central bore, wherein the plate is moveable between an open configuration spaced from the boss to permit mounting and removal of the substrate and a closed position in which the boss projects through the central bore of the plate, to retain the substrate by an edge portion thereof, with the boss causing a central, working portion of the substrate to project outwardly.

13. A sampling apparatus as claimed in claim 12, including a resilient biasing means connected between the plate and the head, biasing the plate into the closed configuration.

14. An apparatus as claimed in claim 13, wherein the substrate comprises a material capable of being subjected to elevated temperatures to vaporize particles thereon.

15. An apparatus as claimed in claim 14, wherein the substrate is chemically inert, is devoid of any dyes and colouring materials, and is such as to be capable of a mechanical wiping action, without removing lints and fibres from the substrate.

16. An apparatus as claimed in claim 15, wherein the substrate is woven and comprises one of cotton, polytetrafluoroethylene, and fibreglass.

17. An apparatus as claimed in claim 16, wherein the substrate has been chemically treated to enhance its ability to collect and entrap at least one of desired particles, droplets and chemical agents, and wherein the substrate has been chemically treated to modify the chemistry thereof during desorption or pyrolysis cycles.

* * * * *